(12) United States Patent
Andersson et al.

(10) Patent No.: US 9,056,304 B2
(45) Date of Patent: Jun. 16, 2015

(54) SPINEL STRUCTURED CATALYST FOR ALDEHYDE PRODUCTION

(75) Inventors: Arne Andersson, Bara (SE); Robert Haggblad, Kavlinge (SE)

(73) Assignee: JOHNSON MATTHEY FORMOX A.B., Perstorp (SE)

( * ) Notice: Subject to any disclaimer, the term of this patent is extended or adjusted under 35 U.S.C. 154(b) by 0 days.

(21) Appl. No.: 13/520,083

(22) PCT Filed: Jan. 19, 2011

(86) PCT No.: PCT/SE2011/000007
§ 371 (c)(1),
(2), (4) Date: Sep. 5, 2012

(87) PCT Pub. No.: WO2011/093763
PCT Pub. Date: Aug. 4, 2011

(65) Prior Publication Data
US 2013/0006019 A1 Jan. 3, 2013

(30) Foreign Application Priority Data
Jan. 26, 2010 (SE) ...................... 1000070

(51) Int. Cl.
| | | |
|---|---|---|
| *C07C 45/38* | (2006.01) | |
| *B01J 23/881* | (2006.01) | |
| *B01J 23/887* | (2006.01) | |
| *B01J 23/00* | (2006.01) | |
| *B01J 35/00* | (2006.01) | |
| *B01J 35/10* | (2006.01) | |
| *B01J 37/03* | (2006.01) | |

(52) U.S. Cl.
CPC .............. *B01J 23/005* (2013.01); *B01J 23/002* (2013.01); *B01J 23/881* (2013.01); *B01J 23/8877* (2013.01); *B01J 35/002* (2013.01); *B01J 35/1009* (2013.01); *B01J 35/1014* (2013.01); *B01J 37/031* (2013.01); *B01J 2523/00* (2013.01); *C07C 45/38* (2013.01)

(58) Field of Classification Search
USPC ........................... 568/471, 474; 502/312, 316
See application file for complete search history.

(56) References Cited

U.S. PATENT DOCUMENTS

| | | | |
|---|---|---|---|
| 3,852,361 | A | 12/1974 | Haas et al. |
| 4,141,861 | A | 2/1979 | Courty et al. |
| 4,220,560 | A | 9/1980 | Anquetil et al. |
| 5,106,811 | A | 4/1992 | Muan et al. |
| 7,193,117 | B2 | 3/2007 | Wachs et al. |
| 7,612,007 | B2 | 11/2009 | Miura et al. |
| 2007/0142677 | A1 | 6/2007 | Olbert et al. |
| 2008/0004173 | A1 | 1/2008 | Miura et al. |

FOREIGN PATENT DOCUMENTS

| | | |
|---|---|---|
| CN | 101096013 | 1/2008 |
| CN | 101500989 | 8/2009 |
| CN | 101564692 | 10/2009 |
| WO | 2010034480 A2 | 4/2010 |

OTHER PUBLICATIONS

Gillot et al., "Analysis of the Diffusion-Induced Stress Effect on the Oxidation in Finely Divided Vanadium Ferrites", Phys. Stat. Sol., 1999, vol. 176, pp. 1047-1060.
Gillot et al., "Cationic distribution and oxidation kinetics of trivalent molybdenum ions in submicron molybdenum substituted magnetites", Solid State Ionics, 1992, vol. 58, pp. 61-69.
Gillot et al., "Effect of the preparation method and grinding time of some mixed valency ferrite spinels on their cationic distribution and thermal stability toward oxygen", Solid State Ionics, 1996, vol. 84, pp. 303-312.
Gillot et al., "New Cation-Deficient Vanadium—Iron Spinels with a High Vacancy Content", Materials Research Bulletim, 1999, vol. 34, Nos. 10/11, pp. 1735-1747.
Nivoix et al., "Intermediate valencies of vanadium cations appearing during oxidation of vanadium—iron spinels", Materials Chemistry and Physics, 2000, vol. 63, pp. 24-29.
Nivoix et al., "Preparation, characterization and reactivity toward oxygen of new nanosized vanadium—iron spinels", Solid State Ionics, 1998, vol. 111, pp. 17-25.
Nivoix et al., "Synthesis and Stability Region of Stoichiometric Nanocrystalline Vanadium—Iron Spinel Powders", Chem. Mater., 2000, vol. 12, pp. 2971-2976.
Nohair et al., "Cationic distribution and mechanism of the oxidation of V3+ ions in vanadium-substituted magnetites", Thermochimica Acta, 1994, vol. 244, pp. 223-234.
Rogers et al., "The Preparation and Properties of Some Vanadium Spinels", J. Phys. Chem. Solids, Pergamon Press, 1963, vol. 24, pp. 347-360.
Wakihara et al., "Preparation and Magnetic Properties of the FeV2O4—Fe3O4 System", Journal of Solid State Chemistry, 1971, vol. 3, pp. 478-483.
Roy et al., "Studies on Thermal Stability of Titanium Substituted Iron Molybdenum Spinel Oxide", Journal of Thermal Analysis and Calorimetry, 2000, vol. 61, pp. 839-847.
Extended European Search Report, dated Oct. 4, 2013, from corresponding EP application.
Chinese Patent Office Search Report, dated Dec. 3, 2013, from corresponding Chinese application.
SE Search Report, dated Jun. 21, 2010, from corresponding SE application.

*Primary Examiner* — Sikarl Witherspoon
(74) *Attorney, Agent, or Firm* — Young & Thompson

(57) ABSTRACT

The present invention refers to a catalyst for aldehyde production, in particular formaldehyde or acetaldehyde production, through selective oxidation of alkanol, especially methanol or ethanol, with oxygen, said catalyst having a spinel structure. The catalyst typically comprises a $Fe^{a+}_q V^{b+}_x Mo^{c+}_y \Delta_z O_4$ spinel structure wherein $\Delta$ is an optional cation vacancy and wherein $z=3-q-x-y$ and $q \times a + x \times b + y \times c = 8$ in concentrations corresponding to $0.6 < q < 3$, $0 \leq x < 1.5$, $0 \leq y \leq 1$ and $0 \leq z < 1.3$ and $2 \leq a \leq 3$, $3 \leq b \leq 5$ and $3 \leq c \leq 6$. The present invention further refers to a process for producing said catalyst and to the use of said catalyst for selective oxidation of alkanol, preferably methanol or ethanol, with oxygen to aldehyde, preferably formaldehyde or acetaldehyde.

20 Claims, 1 Drawing Sheet

Figure 1. X-ray diffraction pattern for sample 3 as prepared.
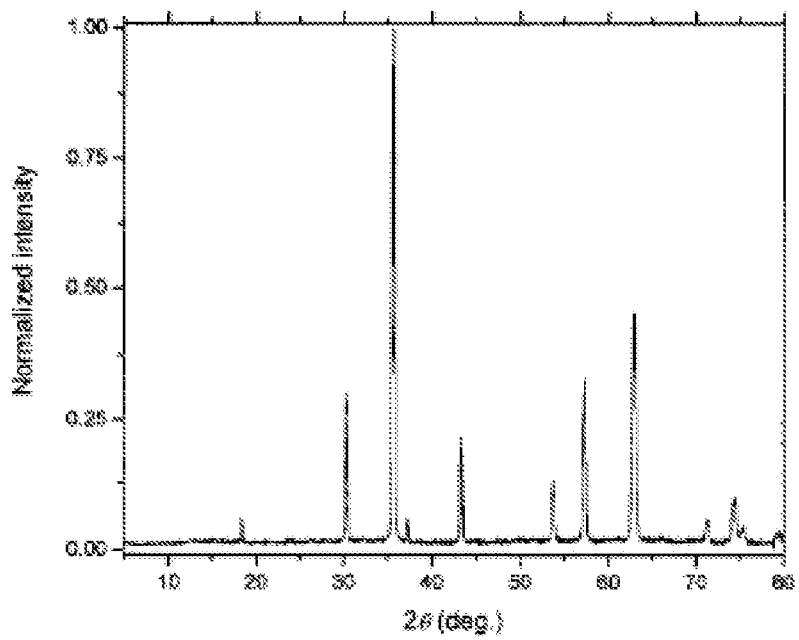
Figure 2. X-ray diffraction pattern for sample 9 as prepared.
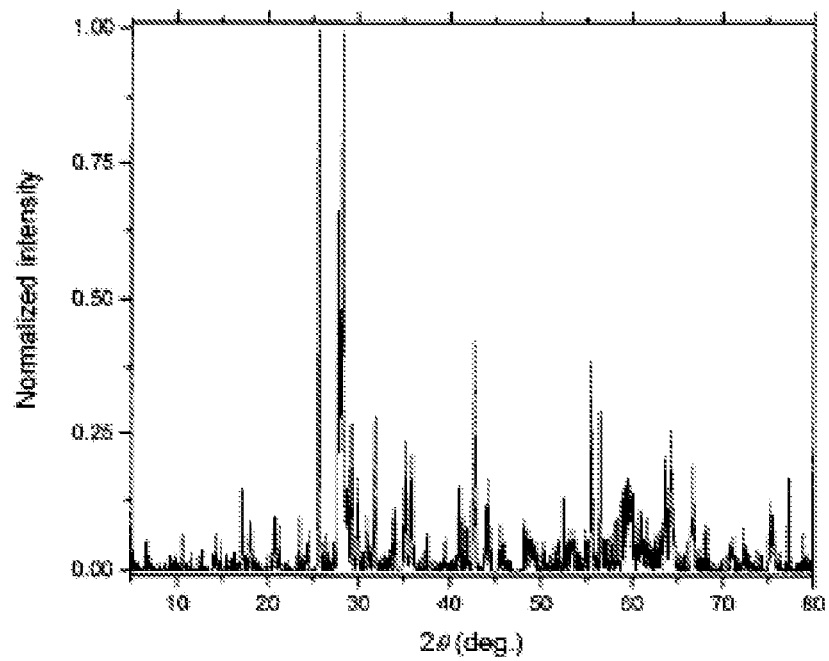

SPINEL STRUCTURED CATALYST FOR ALDEHYDE PRODUCTION

BACKGROUND OF THE INVENTION

FIELD OF THE INVENTION

The present invention refers to a catalyst for aldehyde production, in particular formaldehyde or acetaldehyde production, through selective oxidation of alkanol, especially methanol or ethanol, with oxygen, said catalyst having a spinel structure. In a further aspect, the present invention refers to a process for producing said catalyst and to the use of said catalyst for selective oxidation of alkanol, preferably methanol or ethanol, with oxygen to aldehyde, preferably formaldehyde or acetaldehyde.

DESCRIPTION OF THE RELATED ART

The dominant production method for acetaldehyde today is the Wacker process, which catalyzes the oxidation of ethylene to acetaldehyde. The catalyst is a two-component system consisting of palladium chloride and copper chloride. Prior to the Wacker process acetaldehyde was produced by hydration of acetylene. Converting ethanol into acetaldehyde by catalyzed oxidation is a potential alternative to the Wacker process today due to the increasing availability of ethanol.

Commercial production of formaldehyde from methanol and oxygen is today performed either in the silver- or the metal oxide catalyzed process operated at methanol-rich and methanol-lean conditions, respectively. Historically, due to lower investment costs the silver process has been preferred over the oxide process but as a result of process improvements and increasing methanol prices the more selective oxide process has won market shares and is today the most common choice for new capacities.

In the oxide process, formaldehyde is produced in multi-tube reactors. Typically, a reactor consists of 10-20 000 tubes filled up with ring-shaped catalysts and cooled by oil as heat transfer fluid (HTF). Since the reaction is highly exothermic ($\Delta H = -156$ kJ/mol), isothermal conditions are difficult to obtain and consequently a hotspot is formed at the reaction zone. In order to limit the hot spot temperature, at the first part of the reactor the catalyst can be diluted with inert rings.

The catalyst used in the oxide process is a mixture of iron molybdate $Fe_2(MoO_4)_3$ and molybdenum trioxide $MoO_3$ with a Mo:Fe atomic ratio between 2 and 3. In most aspects the catalytic performance is satisfactory; the plant yield is high (88-93%) and neither molybdenum nor iron are toxic, which is favorable considering both environmental and human health aspects.

However, in methanol oxidation the catalyst suffers from deactivation due to volatilization of molybdenum from the catalyst. Molybdenum sublimes from the upper part of the reactor where the methanol concentration is high and decompose in the lower parts of the reactor, forming needle-shaped $MoO_3$ crystals. As a result of the molybdenum sublimation and condensation/decomposition, the catalytic activity and selectivity to formaldehyde decrease and the pressure drop over the reactor increase. Consequently, after about 1-2 years, or even less than a year, on stream the catalyst has to be replaced depending on the reaction conditions.

To increase the capacity of existing plants and to decrease the size and cost for new plants it is desirable to increase the formaldehyde production per reactor tube and time unit. One possibility doing so is to increase the inlet concentration of methanol. However, as a consequence of higher methanol concentrations, the hot spot temperature might increase since more methanol molecules have to be converted. Since higher temperatures and methanol concentration facilitate the volatilization of molybdenum from the present catalyst, any attempt to increase the plant capacity by increasing the methanol inlet concentration would risk accelerating the volatilization of molybdenum.

Therefore, alternative catalysts showing lower volatility of the active elements are of interest provided that they are active and show comparable selectivity to formaldehyde. Further, due to the concern of environmental and health aspects it is preferable to limit the amount of harmful substances in the catalyst.

According to U.S. Pat. No. 7,193,117 bulk metal vanadates are active and selective as catalysts for methanol oxidation with selectivities to formaldehyde between 89.3% and 96.6% reported at high conversion of methanol. Although these catalysts show high selectivity to formaldehyde, little is known about the stability of the catalysts, in particular the volatility of the vanadium. Further, the amount of toxic vanadium in the catalysts is generally high making them less appropriate as alternatives to commercial $MoO_3/Fe_2(MoO_4)_3$ catalysts.

SUMMARY OF THE INVENTION

An object of the present invention is not only to provide a catalyst suitable for aldehyde production, in particular formaldehyde or acetaldehyde production, through alkanol oxidation, especially methanol or ethanol oxidation. The object is also to provide a catalyst that shows high selectivity to the aldehyde, preferably formaldehyde or acetaldehyde, is stable with low volatility of the active elements and has a limited amount of harmful substances.

This object can be achieved with a catalyst according to the present invention, in which the catalyst has a spinel structure, typically comprising iron, oxygen, vanadium and/or molybdenum. The catalyst preferably comprises a $Fe_q^{a+}V_x^{b+}Mo_y^{c+}\Delta_z O_4$ spinel structure wherein $\Delta$ is an optional cation vacancy and wherein $z=3-q-x-y$ and $q\times a+x\times b+y\times c=8$ in concentrations corresponding to $0.6<q<3$, $0\leq x<1.5$, $0\leq y\leq 1$ and $0\leq z<1.3$ and $2\leq a\leq 3$, $3\leq b\leq 5$ and $3\leq c\leq 6$. The concentrations of, q, x, y and z can further be $1.4\leq q<3$, $0\leq x\leq 1$, $0\leq y\leq 0.3$, $0\leq z\leq 0.9$ or more specifically $0.57<q<3$, $0<x<1.5$, $0\leq y\leq 1$ and $0\leq z<1.29$, $1.33<q<3$, $0<x<1.5$, $0\leq y\leq 1$ and $0\leq z<1$, $0.57<q<3$, $0<x<1$, $0\leq y\leq 1$ and $0\leq z<1.29$, $1.33<q<3$, $0<x<1$, $0\leq y\leq 1$ and $0\leq z<1$, $0.75<q<3$, $0<x<1.5$, $0\leq y\leq 0.3$ and $0\leq z<1.14$, $1.42<q<3$, $0<x<1.5$, $0\leq y\leq 0.3$ and $0\leq z<0.88$, $1.14<q<3$, $0<x<1$, $0\leq y\leq 0.3$ and $0\leq z<0.98$, $1.42<q<3$, $0<x<1$, $0\leq y\leq 0.3$ and $0\leq z<0.88$, $0.57<q<3$, $0\leq x<1.5$, $0<y\leq 1$ and $0\leq z<1.29$, $1.33<q<3$, $0\leq x<1.5$, $0<y\leq 1$ and $0\leq z<1$, $0.57<q<3$, $0\leq x<1$, $0<y\leq 1$ and $0\leq z<1.29$, $1.33<q<3$, $0\leq x<1$, $0<y\leq 1$ and $0\leq z<1$, $0.75<q<3$, $0\leq x<1.5$, $0<y\leq 0.3$ and $0\leq z<1.14$, $1.42<q<3$, $0\leq x<1.5$, $0<y\leq 0.3$ and $0\leq z<0.88$, $1.14<q<3$, $0\leq x<1$, $0<y\leq 0.3$ and $0\leq z<0.98$ or $1.42<q<3$, $0\leq x<1$, $0<y\leq 0.3$ and $0\leq z<0.88$. The catalyst can have cation vacancies in the structure as determined by the deviation from stoichiometry in the spinels, which is determined by the valences of the constituent metals and consequently, the reaction conditions i.e. the reaction temperature and the composition of the reacting gas. Cations of for instance Al, Ca, Co, Cr, Cu, Mg, Mn, Ni, Zn and Ti are also able to form spinel structures with Fe and thus could also be successfully used in catalysts for alkanol oxidation to aldehyde.

This finding, that a catalyst with a spinel structure consisting of a combination of certain concentrations of cations of iron, vanadium and/or molybdenum has all these desired properties, is a quite unexpected effect. Besides showing high selectivity to formaldehyde (>90%) from methanol and oxygen in an inert agent, volatilization of neither vanadium nor molybdenum from the catalyst of the present invention can be detected after 5 days on stream at 300° C. with a flowing gas of 10% methanol and 10% oxygen in nitrogen. Another advantage of the present invention is that highly selective catalysts can be prepared with low vanadium content compared to for instance the catalysts disclosed in U.S. Pat. No. 7,193,117, making the former more appropriate from environmental and human aspects.

The $Fe_q^{a+}V_x^{b+}Mo_y^{c+}\Delta_zO_4$ catalysts are prepared by precipitation from a homogenous water solution containing desired amounts of Fe, V and Mo. The homogenous solution is prepared from one, two or three separate water solutions, containing dissolved $Fe(NO_3)_3.9H_2O$, $NH_4VO_3$ and $(NH_4)_6Mo_7O_{24}.4H_2O$, respectively at appropriate concentrations.

If more than one element is desired in the catalyst, the two or three well stirred solutions are mixed together before homogenization. If necessary, in order to obtain a homogenous mixture of the elements, the solution can be heated and/or the pH can be lowered by adding acids like $HNO_3$, $H_2SO_4$ and/or HCl.

BRIEF DESCRIPTION OF THE DRAWING FIGURES

FIG. 1 depicts the diffractogram for the fresh sample 3.
FIG. 2 depicts the diffractogram for the fresh sample 9.

A solid precipitate is then obtained when pH is sufficiently raised by adding bases such as $NH_3$ and/or NaOH. If necessary, in order to simplify the separation of the solid from the liquid phase by increasing the size of the precipitates the temperature of the liquid containing the precipitate is raised to 35-100° C., typically 40-70° C.

The particles are separated by centrifugation and then washed with water and acetone. As an alternative, the particles are separated by filtration and then washed with water and acetone. The washed particles obtained by centrifugation or filtration are then dried in an oven.

Finally, the dried particles are calcined at temperatures from 300 to 650° C., preferable from 400 to 550° C., in an atmosphere of reducing agents such as $H_2$ and/or CO together with oxidizing agents such as $H_2O$ and/or $CO_2$ in one or more inert agents such as He, Ne, $N_2$, Ar and/or Kr. The gas composition of the reducing, oxidizing and inert agents may vary between 0-50 vol. %, 0-50 vol. % and 99.99-0 vol. %, respectively. The reduction lasts generally for at least three hours. The final catalyst has a specific surface area (BET) of 2-25 $m^2/g$, more preferably 3-10 $m^2/g$, most preferably 4-7 $m^2/g$.

The present invention further refers to the use of said catalyst in a cooled multi-tube reactor for selective oxidation of methanol with oxygen to formaldehyde. In the gas mixture at the inlet of the reactor methanol is present in concentrations of 6 to 13% and oxygen in concentrations of 8 to 15% together with an inert gas, most typically nitrogen. The catalyst of the present invention can be used either alone or together with other catalysts at any position in the reactor.

DETAILED DESCRIPTION OF THE INVENTION

The present invention is further explained with reference to enclosed embodiment examples, which are to be construed as illustrative and not limiting in any way.

Example 1 illustrates the preparation of spinel phase catalysts.

Example 2 is a comparative example illustrating the preparation of a $FeVO_4$ catalyst.

Example 3 illustrates the catalytic performance of spinel phase catalysts.

Example 4 illustrates the ageing of the spinel phase catalysts shown by change in the specific activity and element composition before and after use in methanol oxidation.

Example 5 is a comparative example illustrating the ageing of the triclinic phase $FeVO_4$ catalyst (prepared in Example 2) shown by change the specific activity and element composition before and after use in methanol oxidation.

EXAMPLE 1

Preparation of Spinel Phase Catalysts

With the compositions defined in Table 1, eight samples were prepared by precipitation from a homogenous water solution containing dissolved Fe alone (sample 1) or together with V (sample 2-5) or together with Mo (sample 6-7) or together with both V and Mo (sample 8). The homogenous solution was prepared from one (sample 1), two (sample 2-7) or three (sample 8) separate water solutions, a 0.5 M solution of $Fe(NO_3)_3.9H_2O$ (Merck), a 0.04 M $NH_4VO_3$ (Merck) solution and a 0.5 M $(NH_4)_6Mo_7O_{24}.4H_2O$ (Riedel-de Haën). For preparation of sample 2-8 the two or three well stirred solutions were mixed together and the pH was lowered to 1.0 by adding 3 M $HNO_3$. Also for preparation of sample 1 the pH was lowered to 1.0. After lowering the pH to 1.0 all solutions were homogenous. A solid precipitate then was obtained when the pH was rapidly raised to 4.0 by the addition of 3 M $NH_3$. Particle coarsening was carried out to stimulate the recovery of the particles by heating the turbid solution for 2 hours at 50° C. with maintained stirring. The particles were separated by centrifugation (3000 rpm, 3 min) and then washed three times with water, acetone and again water, respectively. Finally the samples were dried for 16 hours at 80° C. and subsequently reduced for 15 hours at 450° C. in a $H_2/H_2O$/Ar mixed atmosphere.

The phase compositions of the catalysts were determined by X-ray powder diffraction (XRD) analysis on a Seifert XRD 3000 TT diffractometer using Ni-filtered Cu Kα radiation and a rotating sample holder. Data were collected between 5 and 80 degrees 2θ in steps of 0.1° (2.0 seconds/step). As shown in Table 1, all the samples 1-8 were as prepared (denoted fresh) single phase with a $Fe_q^{a+}V_x^{b+}Mo_y^{c+}\Delta_zO_4$ spinel type of structure, similar to $Fe_3O_4$. The diffractogram for the fresh sample 3 is displayed in FIG. 1.

EXAMPLE 2

Preparation of $FeVO_4$ Catalysts

In order to compare samples 1-8 described in Example 1 with a known vanadate catalyst, iron vanadate ($FeVO_4$) disclosed in U.S. Pat. No. 7,193,117 was prepared and denoted sample 9. The preparation procedure was the same as described above in Example 1 except for a different final calcination. Instead of doing the calcination in a reducing atmosphere, the calcination was performed in air at 580° C. for 6 hours. As determined by X-ray diffraction and displayed in FIG. 2, the obtained catalyst was triclinic $(P\bar{1})FeVO_4$.

EXAMPLE 3

Catalytic Performance of Spinel Phase Catalysts

The performance in methanol oxidation of the prepared samples 1-8 of Example 1 was measured in a stainless steal plug flow reactor at 300° C. and atmospheric pressure. To assure isothermal conditions, the reactor was embedded in an aluminum block placed in a tube furnace. Before the measurements the catalyst were ground carefully into fine powder and pressed to tablets, which were crushed sieved into particles with diameters in the range 0.250-0.425 mm. The reactor was loaded with the desired amount of catalyst. The catalyst was heated up to the reaction temperature in a flow of 80 ml/min $N_2$. When the reaction temperature 300° C. was reached, a flow of 10 ml/min of $O_2$ and 10 ml/min gaseous methanol was added to the flow nitrogen. All catalysts were run overnight, and the activities and selectivities obtained after 16 h on stream are presented.

The catalytic activities were determined at low conversion of methanol (<10%) to assure differential conditions, whereas the selectivity data presented are collected at high conversion of methanol (90%). Methanol, formaldehyde (FA), dimethyl ether (DME), methyl formate (MF), dimethoxymethane (DMM) and $CO_2$ were analysed online on a gas chromatograph equipped with a Haysep C column and both an FID and a TCD detector. CO was analysed online on an IR instrument (Rosemount Binos 100). The results are presented in Table 2.

EXAMPLE 4

Ageing of the spinel phase catalysts shown by change in the specific activity and element composition before and after use in methanol oxidation.

Of each sample 1-8 prepared, 0.02 g of catalyst was treated for 5 days at 300° C. in a flow of $N_2$ with 10% methanol and 10% $O_2$. The amount of catalyst was selected to assure differential conversion of methanol (<10%), corresponding to reactor inlet conditions. Previously, it has been reported that the Mo loss is severest at the inlet part of the catalytic bed [A. Andersson, M. Hernelind, O. Augustsson, Catal. Today 112 (2006) 40]. Before (fresh catalysts) and after the treatment (used catalysts), the catalysts were subjected to elemental analysis with ICP-AES. The specific activity of the used samples 1-8 was also measured as described in Example 3. The results of a selection of the samples are presented in Table 3.

EXAMPLE 5

Ageing of the triclinic phase $FeVO_4$ catalyst shown by change in the specific activity and element composition before and after use in methanol oxidation.

Sample 9 was treated as described for sample 1-8 in Example 4 above and subjected to elemental analysis with ICP-AES both as fresh and used. The specific activity of the used sample 9 was also measured as described in Example 3. The results are presented in Table 3.

TABLE 1

Element composition (molar ratio) of prepared catalysts and the phase composition as determined by X-ray diffraction of the prepared catalysts and after 5 days in methanol oxidation (Methanol/$O_2$/$N_2$ = 10/10/80 vol.-% at 300° C.). Samples 1-8 are the Fe—V—Mo-oxide spinel catalysts and sample 9 is the triclinic $FeVO_4$ catalyst.

| | | | | | Phase composition | |
| --- | --- | --- | --- | --- | --- | --- |
| | Composition as designed | | | | Fresh | Used |
| Sample | Formula [a] | V:Fe | Mo:Fe | z range [b] | samples | samples |
| 1 | $Fe_{3.00-z}\Delta_z O_4$ | 0.00 | 0.00 | 0-0.333 | Spinel | Spinel |
| 2 | $Fe_{2.94(1-z/3)}V_{0.06(1-z/3)}\Delta_z O_4$ | 0.02 | 0.00 | 0-0.368 | Spinel | Spinel |
| 3 | $Fe_{2.80(1-z/3)}V_{0.20(1-z/3)}\Delta_z O_4$ | 0.07 | 0.00 | 0-0.447 | Spinel | Spinel |
| 4 | $Fe_{2.00(1-z/3)}V_{1.00(1-z/3)}\Delta_z O_4$ | 0.50 | 0.00 | 0-0.818 | Spinel | Spinel |
| 5 | $Fe_{1.50(1-z/3)}V_{1.50(1-z/3)}\Delta_z O_4$ | 1.00 | 0.00 | 0-1.000 | Spinel | Spinel |
| 6 | $Fe_{2.80(1-z/3)}Mo_{0.20(1-z/3)}\Delta_z O_4$ | 0.00 | 0.07 | 0-0.500 | Spinel | Spinel |
| 7 | $Fe_{2.50(1-z/3)}Mo_{0.50(-z/3)}\Delta_z O_4$ | 0.00 | 0.20 | 0-0.714 | Spinel | Spinel |
| 8 | $FC_{2.50(1-z/3)}V_{0.20(1-z/3)}MO_{0.30(1-z/3)}\Delta_z O_4$ | 0.08 | 0.12 | 0-0.670 | Spinel | Spinel |
| 9 | $FeVO_4$ | 1.00 | 0.00 | 0-0.368 | Triclinic | Spinel |

[a] In the general formula $Fe_q^{a+}V_x^{b+}Mo_y^{c+}\Delta_z O_4$ the number of cation vacancies z is given by the charge balance according to z = 3 − q − x − y and q × a + x × b + y × c = 8.

TABLE 2

Specific activity and selectivity to products for fresh samples 1-8 as measured at 300° C. with a feed consisting of 10% methanol and 10% $O_2$ in $N_2$.

| | Specific activity [a] | Selectivity (%) [b] | | | |
| --- | --- | --- | --- | --- | --- |
| Sample | (µmol/m², s) | FA | DME | MF | $CO_x$ |
| 1 | 1.02 | 0 | 0 | 0 | 100 |
| 2 | 2.33 | 18.3 | 0.4 | 10.3 | 71.1 |
| 3 | 1.60 | 90.6 | 0.9 | 0.9 | 7.6 |
| 4 | 1.63 | 81.9 | 0.7 | 2.4 | 15.0 |
| 5 | 1.42 | 70.1 | 0.6 | 2.5 | 26.8 |
| 6 [c] | 0.90 | 70.8 | 23.5 | 0 | 5.7 |
| 7 [c] | 1.96 | 90.0 | 5.6 | 0 | 4.4 |
| 8 | 0.62 | 83.8 | 4.0 | 6.0 | 6.2 |

[a] Determined at differential conditions (methanol conversion <10%).
[b] Selectivity to the products formaldehyde (FA), dimethyl ether (DME), methyl formate (MF) and carbon oxides ($CO_x$) was measured at 90% conversion of the methanol.
[c] Specific activity and selectivity to products as determined at 10-25% conversion of methanol.

TABLE 3

Composition (molar ratio) of a selection of the catalysts prepared before and after use in methanol oxidation as measured by ICP-AES and the corresponding change in specific activity (activity ratio).

| Sample | Composition as designed [a] | | Fresh catalysts | | Used catalysts [b] | | Activity ratio [c] |
|---|---|---|---|---|---|---|---|
| | V:Fe | Mo:Fe | V:Fe | Mo:Fe | V:Fe | Mo:Fe | |
| 1 | 0 | 0 | 0 | 0 | 0 | 0 | ND |
| 2 | 0.02 | 0 | 0.02 | 0 | 0.02 | 0 | 1.18 |
| 3 | 0.07 | 0 | 0.08 | 0 | 0.08 | 0 | 1.07 |
| 4 | 0.50 | 0 | 0.49 | 0 | 0.54 | 0 | 0.99 |
| 5 | 1.00 | 0 | 1.04 | 0 | 1.04 | 0 | 1.04 |
| 8 | 0.08 | 0.12 | 0.08 | 0.12 | 0.08 | 0.12 | 1.45 |
| 9 | 1.00 | 0 | 0.96 | 0 | 0.89 | 0 | 0.62 |

[a] Composition of the catalysts as designed in the synthesis.
[b] Composition of the catalysts after use in methanol oxidation for 5 days at 300° C. with Methanol/O$_2$/N$_2$ = 10/10/80 vol.-%.
[c] Specific activity of used catalyst divided with specific activity of fresh catalyst.

The invention claimed is:

1. A catalyst, comprising:
   iron, oxygen, and at least metal selected from the group consisting of vanadium and molybdenum, the catalyst having a spinel sructure, the catalyst being adapted by calcination for aldehyde production through selective oxidation of alkanol with oxygen.

2. The catalyst according to claim 1, wherein said catalyst comprises vanadium.

3. The catalyst according to claim 1, wherein said catalyst comprises a Fe$_q^{a+}$V$_x^{b+}$Mo$_y^{c+}$Δ$_z$O$_4$ spinel structure wherein Δ is an optional cation vacancy and wherein z=3−q−x−y and q×a+x×b+y×c=8 in concentrations corresponding to 0.6<q<3, 0≤x<1.5, 0≤y≤1 and 0≤z<1.3 and 2≤a≤3, 3≤b≤5 and 3≤c≤6.

4. The catalyst according to claim 3, wherein 1.4≤q<3.

5. The catalyst according to claim 3, wherein 0≤x≤1.

6. The catalyst according to claim 3, wherein 0≤y≤0.3.

7. The catalyst according to claim 3, wherein 0≤z≤0.9.

8. The catalyst according to claim 1, wherein said aldehyde is formaldehyde and said alkanol is methanol.

9. The catalyst according to claim 1, wherein said aldehyde is acetaldehyde and said alkanol is ethanol.

10. The catalyst according to claim 1, wherein said catalyst has a specific surface area (BET) of 2-25 m$^2$/g.

11. The process for producing a catalyst according to claim 1, comprising:
    precipitating said catalyst from a homogenous water solution containing desired amounts of Fe, V and Mo, where said homogenous solution first is prepared from one, two or three separate water solutions, containing dissolved Fe(NO$_3$)$_3$·9H$_2$O, NH$_4$VO$_3$ and (NH$_4$)$_6$Mo$_7$O$_{24}$·4H$_2$O, respectively, where after said precipitation is obtained by addition of a base to said homogenous solution;
    separating the precipitate from said solution;
    washing the precipitate;
    drying the precipitate; and
    calcining the precipitate at a temperature of 300 to 650° C., in an atmosphere of a reducing agent together with an oxidizing agent in one or more inert agents.

12. A method comprising contacting a catalyst according to claim 1 in a cooled multi-tube reactor for selective oxidation of alkanol, with oxygen to form an aldehyde.

13. The method according to claim 12, wherein said alkanol is methanol and is present in concentrations of 6 to 13% and oxygen in concentrations of 8 to 15% in a gas mixture together with an inert gas, at an inlet of the reactor.

14. The method of claim 12, wherein the alkanol is methanol or ethanol.

15. The method of claim 12, wherein the aldehyde is formaldehyde or acetaldehyde.

16. The catalyst according to claim 1, wherein said catalyst has a specific surface area (BET) of 3-10 m$^2$/g.

17. The catalyst according to claim 1, wherein said catalyst has a specific surface area (BET) of 4-7 m$^2$/g.

18. The method according to claim 13, where the inert gas is nitrogen.

19. The catalyst according to claim 1, wherein said catalyst comprises molybdenum.

20. A catalyst, comprising:
    iron, oxygen, vanadium and molybdenum, the catalyst having a spinel structure, the catalyst being adapted by calcination for aldehyde production through selective oxidation of alkanol with oxygen.

* * * * *